United States Patent [19]

Mehta

[11] Patent Number: 5,877,113
[45] Date of Patent: Mar. 2, 1999

[54] SOLID FORM COMPOSITIONS FOR TREATING NATURAL BODIES OF WATER

[75] Inventor: Raj J. Mehta, King of Prussia, Pa.

[73] Assignee: Organica, Inc., Norristown, Pa.

[21] Appl. No.: 989,346

[22] Filed: Dec. 12, 1997

[51] Int. Cl.$^6$ ............................. C07C 1/02; D06M 16/00; A01N 63/00
[52] U.S. Cl. ......................... 504/117; 435/264; 435/262
[58] Field of Search .................................. 435/262, 264; 504/117

[56] References Cited

U.S. PATENT DOCUMENTS

| | | | |
|---|---|---|---|
| 4,353,800 | 10/1982 | Besik | 210/605 |
| 4,356,092 | 10/1982 | Shimizu et al. | 210/611 |
| 4,421,648 | 12/1983 | Besik | 210/605 |
| 4,678,582 | 7/1987 | Lavigne | 210/150 |
| 4,995,969 | 2/1991 | Lavigne | 210/150 |
| 5,137,625 | 8/1992 | Wolverton | 210/195 |
| 5,171,687 | 12/1992 | Moller et al. | 210/607 |
| 5,286,140 | 2/1994 | Jorgensen et al. | 405/128 |
| 5,340,376 | 8/1994 | Cunningham | 71/6 |
| 5,399,266 | 3/1995 | Hasegawa et al. | 210/615 |
| 5,522,985 | 6/1996 | Bender et al. | 210/150 |
| 5,543,049 | 8/1996 | Hogen et al. | 210/601 |
| 5,554,289 | 9/1996 | Grounds | 435/286 |
| 5,582,732 | 12/1996 | Mao et al. | 210/603 |
| 5,620,893 | 4/1997 | Hogen et al. | 435/262 |
| 5,658,795 | 8/1997 | Kato et al. | 435/252.5 |

*Primary Examiner*—S. Mark Clardy
*Assistant Examiner*—Alton Pryor

[57] ABSTRACT

Solid form compositions for the treatment of natural bodies of water comprising

A) a quantity of beneficial aerobic microorganisms that will control at least one of an organic pollutant, an algae, and a weed in at least a portion of said body of water; and B) a growth accelerator for component A); wherein the solid form composition weighs at least about 85 grams.

20 Claims, No Drawings

SOLID FORM COMPOSITIONS FOR TREATING NATURAL BODIES OF WATER

FIELD OF THE INVENTION

This invention relates to solid form compositions for the treatment of natural bodies of water to control organic pollutants, algae, and/or weeds.

BACKGROUND OF THE INVENTION

Products are available commercially for the treatment of natural bodies of water to control organic pollutants and/or algae therein. Such commercial products are usually based on copper sulfate, or other heavy metal salts, which in turn results in heavy metal contamination of the water.

There is one product on the market known as Organica $^R$ Pond Clarifier, manufactured by Organica Inc. of Norristown, Pa., which is sold in either liquid or water-soluble small particulate sold form. This is a product containing active microbes that preemptively digest the food source in lakes and ponds that supports algae and weed growth. However, while an excellent product, being both biodegradable and non-toxic, this product is not very useful in rivers, streams and other moving bodies of water, including stream fed or spring fed lakes or ponds with outlets, since the dissolved product tends to remain in and move with the water to which it has been added. In addition, even in relatively still bodies of water, the uniform application of this product to bodies of water having large surface areas and/or relatively deep sections is very difficult.

DESCRIPTION OF THE INVENTION

Other than in the operating examples, or where otherwise indicated, all numbers expressing quantities of ingredients or reaction conditions used herein are to be understood as modified in all instances by the term "about".

There has now been discovered a solid form composition that over-comes all of the above drawbacks to the use of the above commercial water treatment compositions.

The solid form compositions of the invention contain

A) an effective quantity of beneficial aerobic microorganisms that will control one or more of algae, weeds, and organic pollutants; and B) an effective quantity of growth accelerators for the component A) microorganisms; wherein the solid form composition weighs at least 85 grams.

The relative quanitites of components A) and B) in the compositions of the invention are dependent in part on the quantity of microrganisms selected for component A). Preferably, component A) will consist of from $1 \times 10^3$ to $1 \times 10^9$ microorganisms per gram of the solid form composition and more preferably from $1 \times 10^4$ to $1 \times 10^8$ microorganisms per gram of the composition. Any quantity of component B) can be present that will effectively accelerate the growth of the microorganisms in component A) when the solid form composition is added to a natural body of water.

Microorganisms that can be used as component A) can be any beneficial aerobic microbial organism or combination of organisms known to control algae, weeds, and/or organic pollutants, and which can survive and function in the aqueous medium provided by natural bodies of water. Such microorganisms include one or more of the following bacteria:

*Bacillus subtilis*
*Bacillus coagulans*
*Bacillus sphericus*
*Bacillus megaterium*
*Bacillus licheniformis*
*Bacillus thurirgensis*
*Bacillus steareothermophilus*
*Bacillus polymyxa*
*Bacillus cereus*
*Bacillus globigi*
*Bacillus halodurans*
*Bacillus azotofixans*
*Bacillus azotoformans*
*Azotobacter sp.*
*Pseudomonas flourescens*
*Pseudomonas aureofaciens*
*Saccharomyces cerevisiae*
*Arthrobacter sp.*
*Flavobacterium sp.*
*Streptomyces sp.*

In addition to bacteria, fungi and viruses can be also used, such as *Aspergillus sp., Trichoderma sp* and/or other beneficial filamentous fungi.

All of the above microorganisms are well known and are readily available from public depositories including ATCC and NRRL.

By the term "control" used herein is meant the elimination or reduction in the quantity of the target contaminant, i.e. algae, weeds, and/or organic pollutants. Algae and weeds are controlled by the preemptive digestion of their food sources. The term "natural bodies of water" includes outdoor bodies of water such as, ponds, lakes, rivers, streams, and brooks, whether naturally occurring or man made, but does not include treatment ponds and tanks for contaminated water from commercial operations such as chemical plants, sewage treatment facilities, and the like.

The organic pollutants that can be controlled by the solid compositions of the invention, which will also result in controlling weeds and algae, if present, include organic plant residues and toxic organic pollutants e.g. pesticides, hydrocarbons, and the like.

The component B) growth accelerators are organic and inorganic compounds that accelerate the growth and reproduction of the component A) microorganisms. Such growth accelerators include carbon sources such as dextrose, sucrose, molassess, and the like, combined carbon and nitrogen sources such as soy proteins, milk amino acids, yeast extracts, and the like; trace elements such as trace metals; and vitamins. In addition, some of the binders and other components used to prepare the finished solid forms may also serve as growth accelerators for the component A) microorganisms.

The solid compositions of the invention are formed by combining components A) and B) into solid forms of the desired shape and weight, i.e. having a weight of at least 85 grams, and preferably from 170 grams to 1.5 kilograms or more. The solid form compositions can be prepared by compression or by the use of suitable molds, preferably using water soluble or dispersible binders that are compatible with the component A) microorganism. Suitable binders include starch (e.g. corn starch), gelatin, sugars such as sucrose, glucose, dextrose, molasses and lactose, and natural and synthetic gums such as acacia, sodium alginate, extract of Irish moss, panwar gum ghati gum, mucilage of isapol husks, carboxmethyl-celluose, methylcellulose, polyvinylpyrrolidone, Veegum$^R$ and larch arabogalacian.

The binders may be present in from 1 to 95% by wieght of the solid composition.

The solid form compositions can be prepared using water as a granulating agent with e.g., pregelatinized starch as a binder. A direct compression method using dry components can also be used, with a binder such as microcrystalline cellulose, microcrystalline dextrose, amylose, or polyvinylpyrrolidone.

In addition to binders, other optional ingredients may also be present, such as lubricants, e.g. sodium benzoate, leucine, magnesium lauryl sulfate, magnesium stearate, calcium stearate, stearic acid, hydrogenated vegetable oils and polyethylene glycol (PEG). Lubricants can be used in from 0.1 to 5% by weight of the composition. One or more disintegrants can also be present such as croscarmelose, crospovidone and sodium starch glycolate, used in from 2% to 4% by weight of the composition. Other optional components include fillers and coloring agents.

Where the microorganisms of component A) are sensitive to light or air or to optional added components, the microorganisms can be separately encapsulated in water soluble coatings, e.g., dyed or undyed gelatin spheres or capsules, or by microencapsulation to a free flowing powder using one or more of gelatin, polyvinyl alcohol, ethylcellulose, cellulose acetate phthalate, or sytrene maleic anhydride. The separately encapsulated microrganisms can then be mixed with the component B) growth accelerators and any optional components. However, encapsulation preferably includes both components A) and B). The resulting capsules can then be mixed with one or more optional components such as binders and formed into the desired solid compositions.

The solid form compositions of the invention can be made in any desired shape such as a golf ball shape, a brick shape, a donut shape, a cylinder, a square, a fish shape, a large golf tee, a large tablet, and the like.

EXAMPLES

Example 1

About $1 \times 10^5$ spore forms of each of the following Bacillus species: *B. licheniformis, B. subtilis, B. sphericus, B. megaterium* and *B. thurirgensis*, per gram of solid composition, are mixed with 90% by weight of microcrystalline amylose, 4% by weight of leucine, 3% by weight of sodium starch glycolate, 1% by weight of glucose, 1% by weight of yeast extract, 0.5% by weight of starch, and 0.5% by weight of soy peptone, and compressed dry in a golf ball shaped mold to produce a golf ball-shaped solid composition weighing about 250 grams.

Example 2

About $1\times10^6$ spore forms of: *Bacillus subtilis* and *Saccharomyces cerevisiae*, and about $1\times10^6$ microencapsulated *Pseudomonas flourescens* microorganisms, per gram of solid composition, are mixed with 83% by weight of pregelatinized starch, 5% by weight of water as a granulating agent, 4.5% sodium benzoate, 4% by weight of crospovidone, 1% by weight of destrose, 1.5% by weight of milk amino acids, and 1% by weight of soy peptone, and compressed in a brick-shaped mold to form a brick-shaped solid composition weighing about 500 grams.

What is claimed is:

1. A solid form composition for the treatment of a natural body of water comprising A) a quantity of beneficial aerobic microorganisms that will control at least one of an organic pollutant, an algae, and a weed in at least a portion of said body of water; and B) a growth accelerating quantity of a growth accelerator for component A); wherein component A) is separately encapsulated inside water soluble coatings or in the form of microcapsules, or wherein both components A) and B) are encapsulated together inside water soluble coatings or are present together in the form of microcapsules.

2. The solid form composition of claim 1 which also contains a water soluble or water dispersible binder.

3. The solid form composition of claim 1 wherein from $1\times10^3$ to $1\times10^9$ microorganisms per gram are present in component A).

4. The solid form composition of claim 1 wherein the microorganisms in component A) are at least one of the following:

*Bacillus subtilis*
*Bacillus coagulans*
*Bacillus sphericus*
*Bacillus megaterium*
*Bacillus licheniformis*
*Bacillus thurirgensis*
*Bacillus steareothermophilus*
*Bacillus polymyxa*
*Bacillus cereus*
*Bacillus globibi*
*Bacillus halodurans*
*Bacillus azotofixans*
*Bacillus azotoformans*
*Azotobacter sp.*
*Pseudomonas flourescens*
*Pseudomonas aureofaciens*
*Saccaromyces cercvisiae*
*Arthrobacter sp.*
*Flavobacterium sp.*
*Streptomyces sp.*
*Aspergillus sp.* and
*Trichoderma sp.*

5. The solid form composition of claim 1 wherein the composition is in the shape of a golf ball.

6. The solid form composition of claim 1 wherein the composition is in the shape of a brick.

7. The solid form composition of claim 1 wherein the composition is in the shape of a donut.

8. The solid form composition of claim 1 wherein the composition is in the shape of a fish. is in the shape of a fish.

9. The solid form composition of claim 1 wherein the composition is in the shape of a large golf tee.

10. The solid form composition of claim 1 wherein component A) controls at least one of an organic plant residue, an algae, and a weed.

11. The solid form composition of claim 1 wherein component B) is at least one source of carbon and nitrogen.

12. The solid form composition of claim 1 wherein component B) contains at least one carbon source and at least one nitrogen source selected from the group consisting of dextrose, sucrose, molasses, soy proteins, milk amino acids, and a yeast extract.

13. The solid form composition of claim 12 wherein component B) also contains at least one vitamin.

14. The solid form composition of claim 13 wherein component B) also contains at least one trace element.

15. The solid form composition of claim 3 wherein from $1 \times 10^4$ to $1 \times 10^8$ microorganisms per gram are present in component A).

16. A method controlling at least one of an organic pollutant, an algae, and a weed in a natural body of water comprising adding to said body of water at least one solid form composition of claim 1.

17. The method of claim 12 wherein the method controls at least one of an organic plant residue, an algae, and a weed.

18. The solid form composition of claim 1 wherein the organic pollutant is an organic plant residue or a pesticide.

19. The solid form composition of claim 1 wherein the solid form composition weighs at least about 85 grams.

20. The solid form composition of claim 1 wherein the solid form composition weighs at least about 170 grams.

* * * * *